United States Patent [19]
Timmons

[11] Patent Number: 5,465,628
[45] Date of Patent: Nov. 14, 1995

[54] MULTIPLE SAMPLING LYSIMETER

[76] Inventor: Robert D. Timmons, R.F.D. Meadowdale Rd., Prairie Du Sac, Wis. 53578

[21] Appl. No.: 305,364

[22] Filed: Sep. 13, 1994

Related U.S. Application Data

[63] Continuation-in-part of Ser. No. 948,520, Sep. 22, 1992, abandoned.

[51] Int. Cl.[6] .................................................. E21B 49/08
[52] U.S. Cl. ..................................... 73/864.34; 73/864.74
[58] Field of Search ............................ 73/863.21, 863.23, 73/864.34, 864.73, 864.74, 155; 175/58–60; 166/264

[56] References Cited

U.S. PATENT DOCUMENTS

| | | |
|---|---|---|
| 2,210,546 | 8/1940 | Hassler . |
| 2,564,198 | 8/1951 | Elkins . |
| 3,490,288 | 1/1970 | Patnode . |
| 4,538,683 | 9/1985 | Chulick . |
| 4,745,801 | 5/1988 | Luzier . |
| 4,759,227 | 7/1988 | Timmons . |
| 4,857,473 | 8/1989 | Magaritz et al. . |
| 5,000,051 | 3/1991 | Bredemeier . |
| 5,035,149 | 7/1991 | Wierenga . |

Primary Examiner—R. Raevis
Attorney, Agent, or Firm—Shlesinger, Arkwright & Garvey

[57] ABSTRACT

A device for selectively extracting fluid samples from a plurality of zones within an underground formation comprising an elongated tube including a wall having internal and external surfaces, the elongated tube having at least one spaced circumferential filter region disposed within the tube wall. The filter region is provided with a circumferential recess portion having an elongated wall extending within the tube external surface. A filter having internal and external surfaces is positioned within the filter region circumferential recess portion such that the elongated wall of the filter region is spaced from the filter internal surface to form a chamber therebetween. The inner surface of the tube has at least one passage opening to the chamber. The passage has a diameter substantially less than the length of the filter and the chamber. A sliding assembly is provided having a pair of sealing balloons and vacuum extraction apparatus. The assembly is selectively positionable about the filter region to seal the same while applying a vacuum to cause a fluid sample to be extracted through the filter and into the assembly.

21 Claims, 2 Drawing Sheets

MULTIPLE SAMPLING LYSIMETER

This application is a continuation of U.S. Ser. No. 07/948,520 filed Sep. 22, 1992, now abandoned.

FIELD OF THE INVENTION

This invention relates to water sampling devices and more particularly to lysimeters and methods of use which provide selective extraction of fluid samples especially from different regions within the vadose zone of an underground formation.

BACKGROUND OF THE INVENTION

The ever increasing problem of toxic landfills and groundwater pollution has necessitated the development of a variety of sampling techniques for locating and tracking the migration of contaminants within underground formations. Conventionally, soil pore water samples are obtained either by the actual extraction of a natural soil sample or through the use of in situ samplers. In the former method, a soil core is collected and pore water is withdrawn from the sample by displacement, compaction, centrifugation, molecular absorption or suction. Conversely, in situ techniques rely primarily upon insertion of a collection vessel within the formation and creation of a vacuum to induce soil pore water flow into a collection vessel. Sampling devices developed for this purpose include vacuum pressure lysimeters, vacuum plates and tubes, membrane filter samplers and absorbent devices.

Generally speaking, most samplers designed for sampling liquids from unsaturated pores may be used to sample from saturated pores as well. However, samplers which are designed for sampling from saturated pores cannot always be used in unsaturated conditions. This is because the liquid in the unsaturated pores is held at less than atmospheric pressure. Further, when sampling in the vadose zone, it is desirable to avoid the actual extraction of the soil sample to the surface. Thus, vacuum or suction samplers commonly known as lysimeters are preferred sampling devices.

Prior art lysimeter probes generally comprise a basic tubular body the end of which has affixed thereto a suction cup, made of porous material, sintered metal or the like which is turned toward the ground. The suction cup itself forms the tip of a lysimeter probe and is mostly cylindrical or conical in shape. The suction cup is fragile as is the basic body which is comprised mostly of plastics or stainless steel. Consequently, the suction cup is sensitive to pressure and is often in danger of being damaged when inserted into the ground. To reduce the likelihood of damage, it has been known to pilot-drill a suitable hole with an auger followed by careful insertion of the lysimeter probe into the pilot-drilled hole. However such drilling is expensive, leads to the possibility of contamination on the surface and causes an undue disturbance to the formation thereby contributing to inaccurate results.

Another problem associated with prior art lysimeter devices is that the soil around the porous section is often so dry that samples cannot be effectively collected. The primary limiting factor under such conditions is the pore size of the lysimeter as well as the hydraulic properties of the soil i.e. the extent of unsaturation. It is therefore extremely important that the filter be in very close contact with the surrounding soil. Lysimeters employing pre-drilled holes do not achieve such close contact and therefore require application of a higher vacuum.

In view of the above, lysimeters which do not require pre-drilled holes have been proposed. These devices may be forcibly driven into the ground with a hydraulic ram or other means. However the forces generated while pounding such devices into the ground often cause damage to the lysimeter. This is especially true of the relatively fragile filter portions that are directly interconnected by threads or other means to the lysimeter body. As a result, hydraulically installed lysimeters have been proposed which provide a solid, sectional rod having fluid passages therethrough. In addition, lysimeters have been proposed which employ balloons to seal off a section of the tube or column so that a vacuum may be applied causing extraction of a fluid sample into the device. For example, U.S. Pat. No. 2,210,546 (Hassler) provides sealing balloons attached to the exterior of the device above and below the filter. Since the filter is not in intimate contact with the soil, sample extraction is not achievable in the vadose zone. Further, balloons create a poor seal against soil.

Still other devices such as U.S. Pat. No. 4,538,683 (Chulick) provide an exterior tube or casing having a screen disposed therein. This device cannot extract fluid samples from unsaturated soils nor is the casing adapted to be hydraulically installed. Fluid extraction requires that multiple concentric tubes be provided and aligned to position the various conduits. The device is both complex in structure and inefficient in operation.

In addition, many conventional lysimeter devices do not have the capability of withdrawing samples from different zones or intervals of the formation being sampled. Prior art sampling is often restricted to a single region location within the soil column. If a sample is desired from a different depth, a separate pilot-drilled hole must be made and the lysimeter must be either lengthened or shortened followed by reinsertion into the new hole. This approach is both time consuming and expensive.

Prior art devices that employ suction to extract the sample often require that a high vacuum be applied because the filter is not intimately in contact with the surrounding soil. Also, the applied vacuum in these prior art devices is not evenly distributed along the entire surface of the filter and therefore results in clogging. Lastly, prior art lysimeters create risks to both personnel and the environment since the drilling process may bring contaminated material to surface.

OBJECTS AND SUMMARY OF THE INVENTION

The present invention is directed to a lysimeter device which can be readily driven directly into the area of interest using hydraulic or pneumatic means without the need for pre-drilled holes and thereby significantly reduce risks to both personnel and the environment from contaminated soil being brought to the surface.

An additional object of the present invention is to provide a single lysimeter device which has a capability of retrieving samples from multiple zones within a single soil column and allows the zones to be changed periodically.

A still further object of the present invention is directed to a vacuum operated lysimeter device for use within the vadose zone which is installed by directly driving the lysimeter into the ground to effect intimate contact between the surrounding soil and the various filter sections.

A still further object of the present invention is to provide a lysimeter device that is driven into the ground without causing damage to the filter sections due to the unique arrangement of the machined tube wall, containing the filter, chamber and passage.

A still further object of the present invention is to provide a lysimeter device which can be selectively lengthened and shortened to allow extraction of samples from depths greater than one hundred feet and through the provision of a wall structure including a unique chamber adjacent the filter to enable the vacuum to be evenly distributed and established across the entire inner surface of the filter.

A further object of the present invention is to provide a lysimeter device whereby the filter sections are interfit into the body portion by close abutment rather than interconnection thereby lessening their susceptibility to shock.

Yet another object of the present invention is to provide a lysimeter device that eliminates the need for silica flour packing within the bore hole or use of other hydrophilic material normally required for vadose zone sampling since the lysimeter tube is directly inserted into the formation for intimate contact between the filter and soil.

A still further object of the present invention is to provide a lysimeter device which because of its ability to be hydraulically or pneumatically installed, will quickly and economical extract a sample and minimize contamination spread to the surface as compared to the prior art.

A further object of the present invention is to provide a hydraulically or pneumatically installed lysimeter device having a smooth and uniform diameter throughout thereby allowing the device to be readily inserted into the ground and removed from the formation with less resistance after the sample is extracted leaving only a small diameter hole which can be conveniently plugged.

Another object of the present invention is to provide a lysimeter device that increases sample reliability and decreases sample contamination through the provision of a chamber adjacent the filter that may be readily backflushed during the period between sample extractions.

Yet another object of the present invention is to provide a lysimeter device adapted for use in a variety of soil textures and moisture and with a minimum of filter pore plugging since the device is directly driven into the ground.

Yet another object of the present invention is to provide a lysimeter device capable of being inserted within an underground formation at an angle between about 0° and 60° from the vertical.

A still further object of the present invention is to provide a lysimeter device having modular construction, each subsection of which is available in a variety of lengths that are readily interconnected to provide a rigid metal tube having the structural stability required for insertion into the ground.

Another object is to provide a lysimeter for hydraulic installation having a unique wall structure to house the fragile filter and allow the device to be forcibly driven into the formation with no damage to the filter.

A further object is to provide a device for establishing a sampling column into a formation comprising easily assembled subsections that include intermittent filters secured to the device by abutment between two adjacent subsections.

These and other objects of the invention are achieved by providing a device for selectively extracting fluid samples from a plurality of zones within an underground formation comprising an elongated tube including a wall having internal and external surfaces, the elongated tube having at least one spaced circumferential filter region disposed within the tube wall, the filter region provided with a circumferential recess portion having an elongated wall extending within the tube external surface. A filter having internal and external surfaces is provided, the filter is positioned within the filter region circumferential recess portion so that the filter external surface and the tube cooperate to form a substantially uniform outside diameter to the tube. The elongated wall of the filter region is spaced from the respective filter internal surface and forms a chamber therebetween. The inner surface of the tube has at least one passage opening into the chamber. The passage has a diameter substantially less than the length of the filter and the chamber. A device slidable within the tube and selectively positionable about the at least one filter region is provided. A device for sealing the at least one filter region is also provided and associated with the slidable device to allow extraction of a fluid to be sampled through the at least one filter region by applying a negative pressure thereto when the lysimeter is disposed within an underground formation.

A further object is to provide a device for insertion into an underground formation to establish a sampling column for the purpose of enabling the extraction of fluid samples therethrough comprising a plurality of individual tubular subsections interconnected in an end to end relation to form a length of elongated tube having a longitudinal axis and defining a continuous wall provided with internal and external surfaces. At least one of the tubular subsections has an exterior portion thereof reduced in diameter for a distance along the length of the reduced diameter subsection to at least one end thereof to provide a circumferential recessed portion having an elongated recessed wall extending within the continuous wall external surface of the tube. A filter having internal and external surfaces and first and second ends is provided, the filter being positioned within the circumferential recessed portion whereby one of the filter ends abuts against the end of an adjacent one of the interconnected individual tubular subsections. The filter exterior surface and the elongated tube wall external surface cooperate to form a substantially uniform outside diameter to the tube. The elongated recessed wall is spaced from the respective filter interior surface and forms a chamber therebetween. The tube wall interior surface has at least one passage opening into the chamber whereby selective application of a vacuum within the interior of the elongated tube causes a fluid sample to be extracted through the filter and into the interior of the elongated tube.

DESCRIPTION OF THE PREFERRED EMBODIMENT

Figure 1:
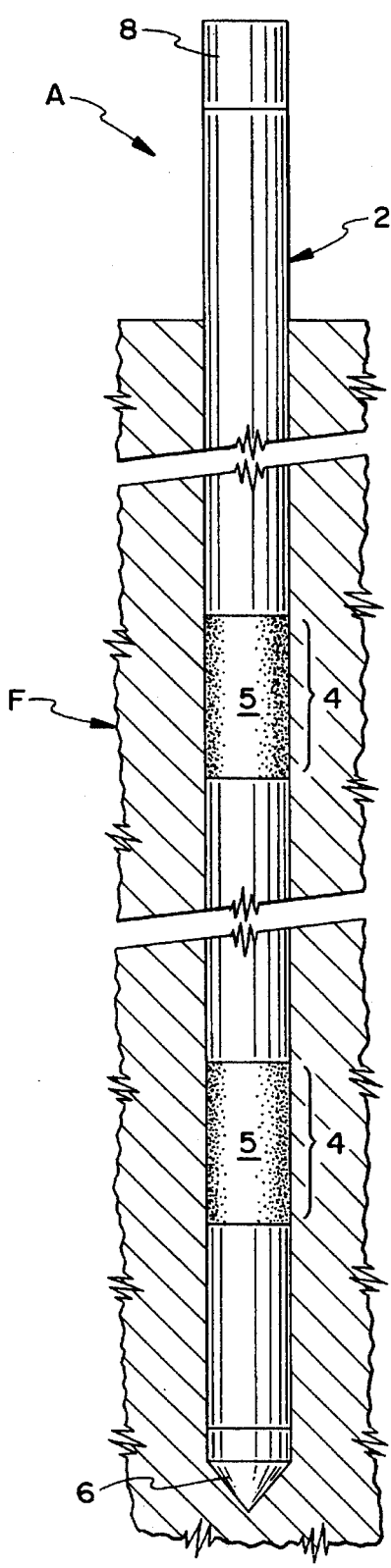
FIG. 1 illustrates the lysimeter device according to the present invention installed within an underground formation.

Referring to FIG. 1, the lysimeter device A according to the present invention is shown inserted within a vadose zone or other region of an underground formation F. The lysimeter device A comprises an elongated, generally tubular member or body portion 2 having filter sections 4 which include filters 5 extending circumferentially around the perimeter of the body portion 2 at various intervals along its length. In the preferred embodiment, the body portion 2 comprises a number of individual, interfitting subsections which are secured together by threaded portions or other suitable connection means to a desired length.

The amount of spacing between distinct filter sections 4 depends upon the desired depth to be sampled. It is within the scope of the present invention to construct the body portion 2 in a variety of diameters and from a variety of materials however in the preferred embodiment the body portion 2 will have an inside diameter of about one inch and each of the various subsections will be constructed from stainless steel.

A drive point 6 is provided at one end of the body portion 2 while a drive cap 8 is provided at the opposite end thereof. The drive point 6 and the drive cap 8 may be respectively threaded onto the ends of the body portion 2 or secured in some other manner. The drive point 6 and the drive cap 8 are likewise constructed from stainless steel. The overall stainless steel construction of the body portion 2 enables the device to be directly and forcibly inserted into a formation by either a pneumatic or hydraulic means without the need to produce a pre-drilled hole. Other high strength metals and materials may be used.

Figure 2:
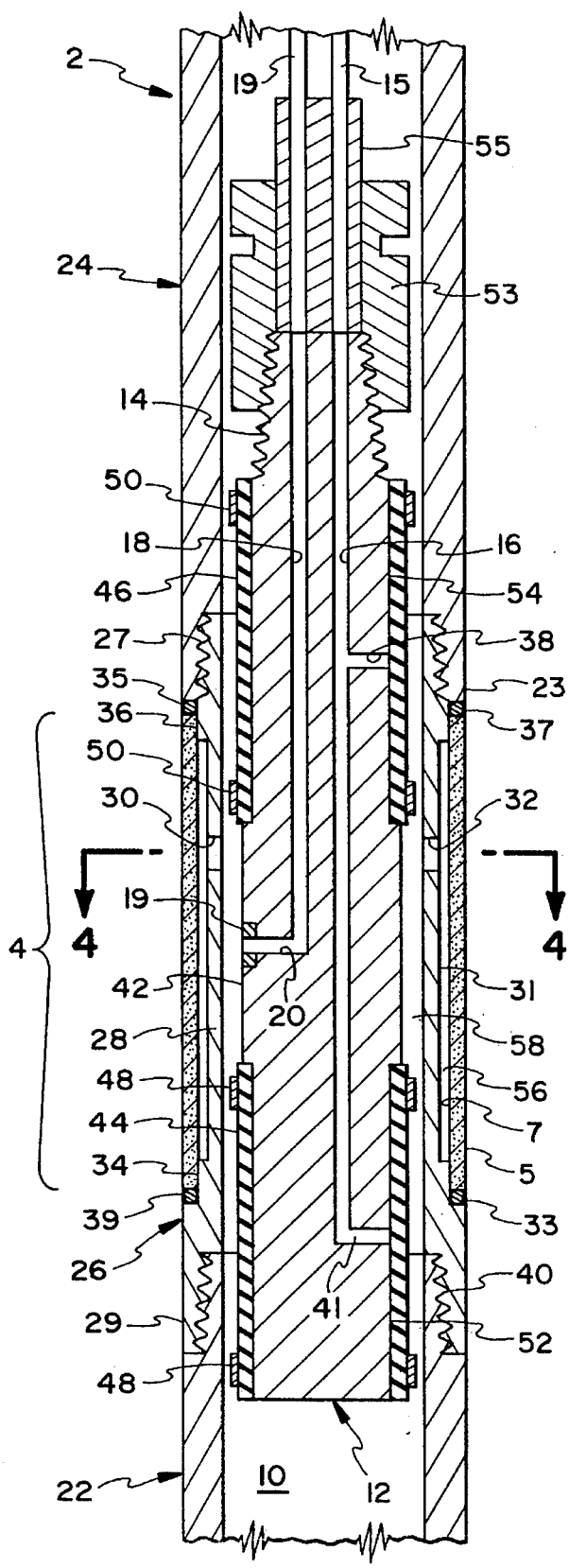
FIG. 2 is an enlarged vertical cross sectional view of the device shown in FIG. 1 with portions broken away and showing the sampling assembly positioned within the body portion and the sealing means in the deflated position.
Figure 4:
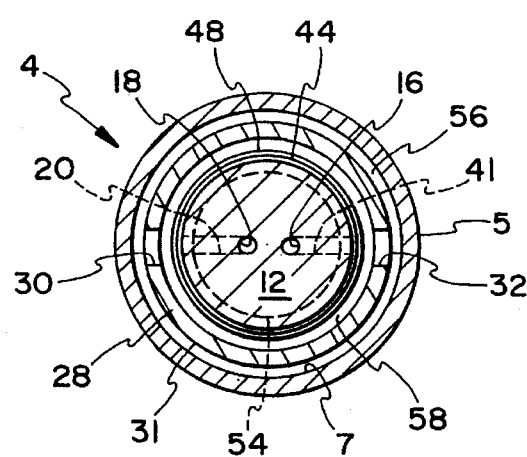
FIG. 4 is a horizontal cross-sectional view of the device taken along lines 4—4 of FIG. 2.

Turning now to FIGS. 2 and 4, the lysimeter device A is illustrated in greater detail. Three separate subsections 22, 24 and 26 are shown interconnected with intermediate subsections 26 positioned between 22 and 24. The connected subsections create a length of elongated tube 2 having an interior passageway 10. It is within the scope of the present invention to provide interconnection between the various subsections 22, 24 and 26 by other than the male and female threads shown. The essential requirement according to the present invention is that each of the various subsections 22, 24 and 26 interfit to form a unitary and structurally sound elongated tube 2. The requirement of structural integrity between the various subsections is critical since the device is forcibly pushed or driven into the formation and must therefor absorb and distribute the shock of impact through the subsections without loosening or causing damage to the more fragile portions of the lysimeter A.

Intermediate subsection 26 comprises a first end portion 27, second end portion 29 and a mid portion 28 disposed therebetween. Mid portion 28 has an exterior diameter less than second end portion 29 as does first end portion 27. First end portion 27 includes male threads for engagement with female threads of end portion 23 associated with subsection 24. The second end portion 29 of intermediate subsection 26 includes female threads for engagement with male threads of end portion 40 on subsection 22. Thus, a great number of interconnected subsections 22, 24 and 26 may be provided to create an overall elongated tube 2 having spaced circumferential filter regions 4 disposed along its length.

As best shown in FIG. 2, the circumferential filter region 4 contains and supports a filter 5 that extends longitudinally along tube 2 from a first recess or shoulder portion 36 to a second recess or shoulder portion 34 at an opposite end thereof on intermediate subsection 26. The filter region 4 may extend around the perimeter of the tube 2 as best shown in FIG. 4. An elongated recessed surface or wall portion 31 extends within the exterior surface of mid portion 28 and below the first and second shoulder portions 36 and 34. As shown in FIG. 4, wall 31 also extends 360° around mid portion 28 and together with the interior surface 7 of a filter 5 creates a continuous elongated chamber 56 extending the perimeter of tube 2. A pair of bores, passageways or passages 30 and 32 extend through the mid portion 28 and wall 31 to provide an opening between chamber 56 and the interior 10 of the tube 2. Additional passages may be provided as required.

The filter 5 is positioned within the filter region 4 of tube 2 so that the first filter end 37 is supported by first shoulder 36 and abuts against the bottom surface of subsection 24 end portion 23. The opposite, second end 33 of filter 5 is supported by second shoulder 34 of intermediate subsection 26. It is therefore apparent that when subsections 24 and 26 are threadedly engaged, the filter 5 is firmly held within filter region 4 and forms a substantially uniform outside diameter with elongated tube 2. The filter 5 supported in second shoulder 34 abuts at first end 37 against the bottom of subsection 24 end portion 23. As can be appreciated, if only one or two formation depths are to be sampled, only one or two intermediate subsections 26 are required.

A pair of annular gaskets or seals 35 and 39 are provided within filter region 4 to seal the filter 5 therein. Gasket 35 is shown positioned between first filter end 37 and the bottom surface of subsection 24 end portion 23. The opposite, second end 33 of filter 5 is similarly provided with a gasket 39 disposed within shoulder 34. The gaskets 35 and 39 may be constructed from TEFLON (polytetrafluoroethylene), neoprene or other elastomeric compounds which are stable, chemical-resistant and inert. Other materials are within the scope of the present invention so long as they provide an effective fluid-tight seal and are non-leachable. Each gasket has a thickness of about 1/32" to about 1/8".

Filter 5 may be constructed from a variety of materials having a porosity such that fluid, for example water or gas, is allowed to pass through while undesirable solids such as soil or other grain minerals do not. Suitable filter material according to the present invention includes ceramic, stainless steel and TEFLON (polytetrafluoroethylene) among others. One preferred filter material is constructed from porous fluoroplastic resins as set forth in U.S. Pat. No. 4,759,227 which is incorporated herein by reference. Other filter materials may be employed so long as they efficiently allow transmission of liquids or gases while at the same time providing a sufficient barrier against soil or other undissolved materials without undue clogging.

Because the relatively fragile filter 5 of the present invention does not provide structural support in the manner of the subsections 2, it will neither transmit nor receive an inordinate amount of force as the lysimeter A is driven into the ground. The forces produced by impact of the hydraulic ram against the cap 8 are primarily transmitted and absorbed by the threadedly connected stainless steel subsections 22, 24 and 26. Thus, the present invention is able to provide a hydraulically inserted lysimeter tube having a substantial filter area 4 of relatively fragile porous material within the wall of the lysimeter. Since the exterior surface of the filter 5 remains flush with the exterior surface of various subsections 22, 24 and 26 contact between the filter 5 and the surrounding soil is maximized as the device is inserted within a formation. This intimate contact between the soil and filter eliminates the need for hydrophilic packing material required by prior art devices and decreases the amount of vacuum required to be applied. Finally, the provision of a chamber 56 adjacent to the filter 5 increases the vacuum through the filter 5 without weakening the wall of the tube 2. The chamber 56 and filter 5 are incorporated within the tube 2 without reducing the inner diameter of the tube while maintaining a uniform tube outer diameter. This ensures the device is readily inserted in the ground and the sliding assembly 12 is freely movable within the interior 10 of tube 2.

Returning to FIG. 2, a sliding, sampler assembly 12 is shown disposed within the interior passageway 10 of the tubular body portion 2. The sampler assembly 12 has a threaded portion 14 at one end thereof and further includes air passageway 16 and vacuum passageway 18. Both the air passageway 16 and the vacuum passageway 18 are centrally disposed within the sampler assembly 12. The air passageway 16 further includes a first outlet 38 and a second outlet 41 each of which branches off of the air passageway 16 at opposite ends of the sampler assembly 12. The vacuum passageway 18 is shown provided with a vacuum outlet 20 branching laterally off of the passageway 18 through side wall 42 of the sampler assembly 12. The first air outlet 38 and second air outlet 41 are shown generally positioned adjacent the ends of the sampler assembly 12 while vacuum outlet 20 is positioned central to the sampler assembly 12. It is within the scope of the present invention to provide additional air and vacuum outlets or to shift their relative locations as required.

A sealing device comprising a pair of inflatable bladders 44 and 46 is provided on sampler assembly 12. Inflatable bladder 46 is positioned at a first end of the sampler assembly 12 so as to form a circumferential seal about air outlets 38. The other inflatable bladder 44 is positioned on the sampler assembly 12 at an opposite end thereof to form a seal around the remaining outlet 41 in a similar manner. A preferred material for inflatable bladders 44 and 46 is Viton®, however any of the resilient and expandable resins or rubbers known in the art are contemplated as being within the scope of the present invention. The primary requirement is that the inflatable bladders 44 and 46 are resilient, readily expandable upon inflation and form a fluid tight seal within the interior 10 of body 2.

A pair of stainless steel clamps 48 and 50 secure the inflatable bladders 44 and 46 to the sampler assembly 12 to effect an airtight seal and allow the bladders to be inflated. Sampler assembly wall regions 52 and 54 are shown having a reduced diameter from that of side wall region 42. This configuration enables the inflatable bladders 44 and 46 to be positioned around the sampler assembly 12 yet maintain clearance from interior 10 when uninflated. Sufficient clearance between the uninflated bladders 44 and 46 and interior passageway 10 minimizes friction with the surface of the interior passageway 10 as the sampler assembly 12 is moved therethrough.

An adapter 53 is shown threadedly or otherwise connected to the end 14 of the sampler assembly 12 and secures stainless steel connector tube 55 to vacuum line 19 and compressed air line 15. As can be appreciated, once the adapter 53 is threaded onto the end 14 of the sampler assembly 12, air passageway 16 is aligned with and connected to air line 15 and the vacuum passageway 18 is connected to the vacuum line 19. Also provided is a compressed air pump (not shown) and a vacuum pump (not shown) connected to the respective fluid lines. In a preferred embodiment, the vacuum line 15 is constructed from TEFLON (polytetrafluoroethylene) tubing having a rigidity sufficient to conduct a vacuum therethrough. The air line 15 may be constructed from relatively flexible nylon tubing or other suitable material.

A microelectronic sensor 19 may be incorporated within sampler assembly 12 at inlet 20 or another locations. The sensor transmits data to the surface once it comes in contact with a fluid that is chemically toxic or radioactive. For example, the sensor 19 could measure the resistivity of the fluid and the data is then transmitted to an appropriate computer unit (not shown) at the surface. Computer analysis of the resistance reading would indicate the presence of specific toxic compounds in the sample and an appropriate warning could be provided for the operator. The sensor 19 may transmit the data via radio signal or appropriate wiring incorporated within the vacuum lines 19 to the computer unit. Other arrangements are envisioned within the scope of the present invention for design of the safety sensor so long as it provides reliable transmission of the information to the surface.

In operation, the tubular body portion 2 is assembled to the required length by threadedly connecting a number of subsections 22, 24 and 26 having filters 5 disposed along their length. Each filter region 4 corresponds to a different depth from which to extract a sample. Generally speaking, the body portion 2 may be assembled in lengths up to about twenty feet. However, by incorporating a suitable transfer vessel, samples may be taken from depths beyond twenty feet and up to about one hundred feet.

Once the body portion 2 is assembled having filter regions 4 at desired intervals, a drive point 6 and drive cap 8 are secured to the respective ends of the tubular body portion 2. The lysimeter device A is then pushed or otherwise driven into the underground formation F or vadose zone in a direction generally illustrated in FIG. 1. In the preferred embodiment, a hydraulic device (not shown) will be used to impact against the drive cap 8 to push the drive point 6 into the underground formation F thereby guiding the lysimeter device A to the required depth. As will be appreciated, other types of pushing or driving forces may be employed in accordance with the present invention including pneumatic means or other mechanical devices. An auger or other drilling device is not required to provide a pre-drilled hole since the assembled lysimeter device A can readily withstand the forces of impact without causing damage to the filters 5.

Once the lysimeter device A has been inserted into the formation and at the required depth, the drive cap 8 is removed from the end of the body portion 2 and the sampler assembly 12 is positioned within the interior passageway 10 of the tubular body portion 2. The sliding sampler assembly 12 is caused to descend into the interior passageway 10 until it is adjacent a filter region 4 such that inflatable bladders 44 and 46 are disposed above and below passages 30 and 32 of intermediate subsection 26. Once positioned, the air line 15 is supplied with compressed air from a suitable pump or compressor (not shown) to provide a flow of compressed air into passageway 16 and out first air outlet 38 and second air outlet 41 causing bladders 44 and 46 to expand.

Figure 3:
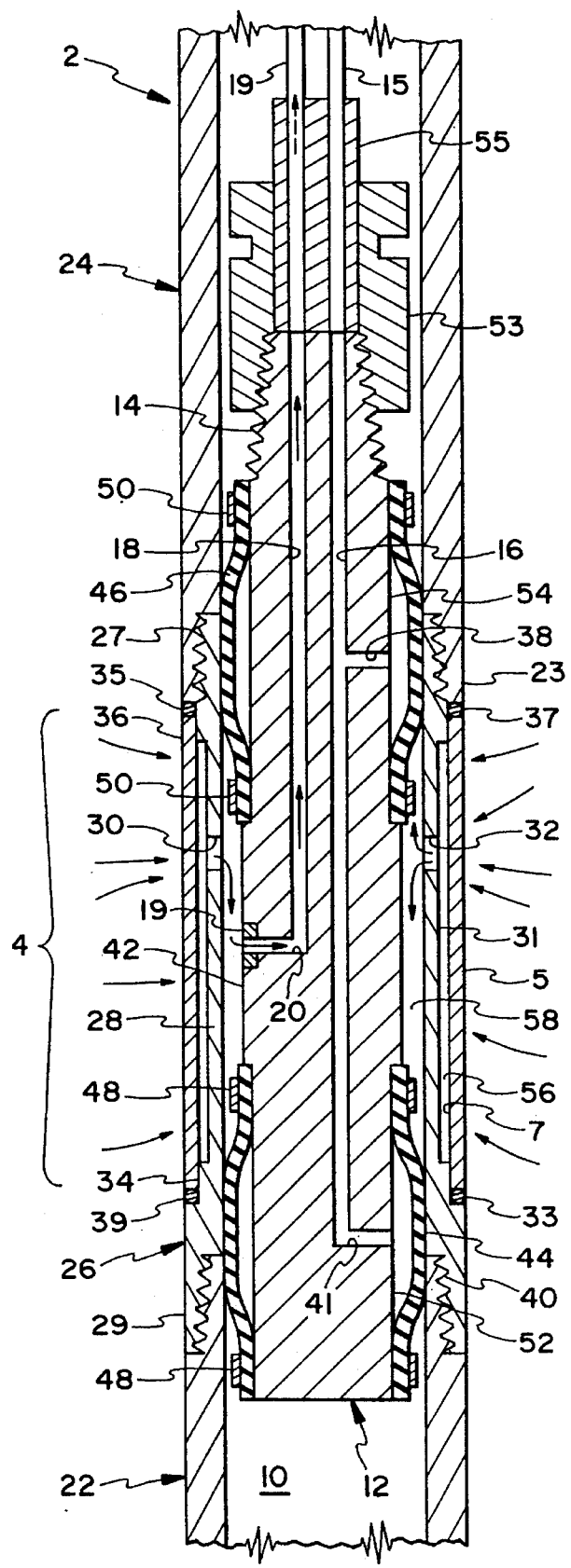
FIG. 3 illustrates the device shown in FIG. 2 having the sealing means in the inflated position and with arrows indicating the flow path of a fluid sample from the soil, through the filter and into the sampling assembly.

As best shown in FIG. 3, the supply of compressed air into air passageway 16 of the sampler assembly 12 causes inflation and expansion of bladders 44 and 46 into a fluid tight sealed position against the surface 10 of tube 2. While the sampling device 12 is in this "sealed" mode, the vacuum pump (not shown) is activated and a vacuum or negative pressure is created within vacuum line 19, vacuum passageway 18 and inlet 20. The high vacuum forces continue through passages 30 and 32 and into chamber 56 adjacent filter 5. This vacuum causes fluid from the surrounding formation to be directly drawn from the surrounding soil and through the length of filter 5 in the direction indicated by the arrows. Positioning of chamber 56 adjacent the interior surface of the filter 5 will allow the fluid to be extracted along the entire length of the filter. The chamber 56 also helps reduce pore clogging of the filter 4 by evenly distributing the vacuum along the filter surface 7. The filtered liquid sample continues into chamber 56 and through passages 30 and 32 for eventual withdrawal to the surface via passageway 18 or, if operating at a depth beyond twenty feet, to a suitable transfer vessel (not shown).

Once a sufficient liquid sample has been extracted, the vacuum and compressor pumps (not shown) may be turned off and the inflated bladders 44 and 46 are allowed to deflate back into the position shown in FIG. 2. If desired, the present invention allows the filter region 4 and associated structure to be backflushed with a rinsing fluid prior to extraction of a different sample. This reduces the likelihood of contamination between different samples. Fluid will be forced via positive pressure into vacuum passageway 18 causing it to fill chamber 56 and pass out of filter 5 into the formation thereby backflushing all fluid passages and cleaning the filter.

The bladders 44 and 46 are again deflated and the sliding sampler assembly 12 is repositioned adjacent the next filter region 4 to be used. After repositioning, the inflatable bladders 44 and 46 are reinflated and a vacuum is reapplied to extract a new sample from a different depth. In this way different samples can be withdrawn from different depths without the need for removing the entire lysimeter device A from the formation F. Once all the samples have been collected, the sliding sampler assembly 12 is withdrawn from the interior passageway 10 of the body portion 2 and the entire body portion 2 is removed from the formation F.

As is apparent, the elongated tube 4 may be disassembled to clean or replace a filter 5 or simply to relocate the filter section 4.

While the invention has been disclosed as having a preferred design, it is understood that it is capable of further modifications, uses and/or adaptations of the invention following in general the principle of the invention and including such departures from the present disclosure as come within known or customary practice in the art to which the invention pertains, and as may be applied to the central features hereinbefore set forth, and fall within the scope of the invention of the limits of the appended claims.

I claim:

1. A device for selectively extracting fluid samples from a desired zone within an underground formation comprising:
    a) an elongated tube including a wall having internal and external surfaces;
    b) said elongated tube having at least one spaced circumferential filter region disposed within said tube wall;
    c) said at least one filter region provided with a circumferential recess portion having an elongated wall extending within said tube external surface;
    d) said at least one filter region including a filter having internal and external surfaces, said filter positioned within said at least one filter region circumferential recess portion;
    e) said filter external surface and said tube cooperating to form a substantially uniform outside diameter portion of said tube whereby said outside diameter portion provides means for contacting the formation when fluid samples are extracted;
    f) said elongated wall of said at least one filter region is spaced from said respective filter internal surface forming a chamber therebetween;
    g) said internal surface of said elongated tube having at least one passageway extending therethrough and opening to said chamber;
    h) means slidable within said elongated tube and selectively positionable about said at least one filter region for sealing said at least one filter region from the remainder of said elongated tube; and
    i) means associated with said slidable means for extracting a fluid sample through said at least one filter region by applying a vacuum thereto when said elongated tube is disposed within an underground formation.

2. A device as in claim 1 and further comprising:
    a) a drive point for guiding said elongated tube as it is pushed into the underground formation to be sampled.

3. A device as in claim 2 and further comprising:
    a) a drive cap member to provide a point of contact when driving said elongated tube into the underground formation to be sampled.

4. A device as in claim 3 and wherein:
    a) said elongated tube, said drive point and said drive cap are constructed from stainless steel.

5. A device as in claim 1 and wherein:
    a) said filter is constructed from a material selected from the group consisting of ceramic, polytetrafluoroethylene and stainless steel.

6. A device as in claim 1 and wherein:
    a) said slidable means including a bladder means expandable into a sealing position about said at least one filter region and against said elongated tube internal surface.

7. A device as in claim 6 and wherein:
    a) said bladder means including first and second inflatable bladders disposed on said slidable means so that when said first inflatable bladder is selectively positioned above said filter region said second inflatable bladder is positioned below said filter region.

8. A device as in claim 6 and wherein:
    a) said slidable means including at least one fluid line for selectively directing an inflation fluid into said bladder means to inflate the same.

9. A device as in claim 1 and wherein:
    a) said fluid extracting means including at least one vacuum line associated with said slidable means and movable therewith within said elongated tube internal surface for positioning about said at least one passageway.

10. A device as in claim 1 and wherein:
    a) said slidable means is constructed from polytetrafluoroethylene.

11. A device as in claim 1 and wherein:
    a) said elongated tube comprising a series of interconnected, tubular subsections.

12. A device as in claim 11 and further comprising:
    a) interconnecting means associated with said subsections.

13. A device as in claim 12 and wherein:
    a) said at least one filter region comprising a reduced diameter tubular subsection having a first end and a second end, said reduced diameter tubular subsection first end is secured to one of said series of tubular subsections to form said circumferential recess portion.

14. A device as in claim 13 and wherein:
    a) said reduced diameter tubular subsection first end has a diameter substantially less than that of said one of said series of tubular subsections to which it is attached and forms a first annular shoulder portion within said elongated tube; and b) said reduced diameter tubular subsection second end has a diameter similar to that of another of said series of tubular subsections to which it is attached, said reduced diameter tubular subsection second end includes a second annular shoulder portion disposed therein, said second annular stepped shoulder portion having a diameter equal to that of said first annular shoulder portion thereon.

15. A device as in claim 14 and wherein:

a) said filter has a cylindrical shape and is supported at a first filter end by said first annular shoulder portion and at an opposite end thereof by said second annular shoulder portion.

16. A device as in claim 13 and wherein:

a) said at least one passageway extending perpendicular through said internal surface of said elongated tube and having a diameter substantially less than the length of said filter and said chamber.

17. A device as in claim 13 and wherein:

a) said reduced diameter tubular subsection first end provided with male threads and said reduced diameter tubular subsection second end provided with female threads to allow said reduced diameter tubular subsection to be threadedly engaged to said one of said series of tubular subsections and said another of said series of tubular subsections respectively.

18. A device as in claim 1 and wherein:

a) said chamber has a length and width substantially equal to said filter internal surface.

19. A device as in claim 1 and further comprising a) means for sensing the fluid sample during extraction to identify the constituents therein.

20. A device as in claim 1 and wherein:

a) means for sealing said at least one filter within said respective at least one filter region.

21. A device as in claim 20 and wherein:

a) said sealing means including elastomeric o-rings positioned within said circumferential recess portion to provide a fluid-tight seal between said at least one filter and said respective circumferential recess portion.

* * * * *